(12) United States Patent
Shindo

(10) Patent No.: US 7,780,975 B2
(45) Date of Patent: Aug. 24, 2010

(54) BIOMATERIAL HAVING APATITE FORMING ABILITY

(75) Inventor: Toyohiko Shindo, Tokyo (JP)

(73) Assignee: Contamination Control Services, Tokyo (JP)

( * ) Notice: Subject to any disclaimer, the term of this patent is extended or adjusted under 35 U.S.C. 154(b) by 2051 days.

(21) Appl. No.: 10/645,073

(22) Filed: Aug. 21, 2003

(65) Prior Publication Data

US 2004/0131652 A1 Jul. 8, 2004

(30) Foreign Application Priority Data

Aug. 27, 2002 (JP) .............................. 2002-246678
Jun. 27, 2003 (JP) .............................. 2003-184848

(51) Int. Cl.
*A61F 2/28* (2006.01)

(52) U.S. Cl. ...................................................... 424/426

(58) Field of Classification Search ........................ None
See application file for complete search history.

(56) References Cited

FOREIGN PATENT DOCUMENTS

| JP | 62-34559 | 2/1987 |
|---|---|---|
| JP | 2-13580 | 4/1990 |
| JP | 03-097466 | 4/1991 |
| JP | 04-035668 | 2/1992 |
| JP | 09-157528 | 6/1997 |
| JP | 09-157594 | 6/1997 |
| JP | 09-183665 | 7/1997 |
| JP | 2002-105676 | 4/2002 |
| JP | 2002-114858 | 4/2002 |
| JP | 2002-114859 | 4/2002 |
| JP | 4017836 | 12/2007 |
| WO | WO2004039904 | * 4/2004 |

OTHER PUBLICATIONS

BESIM BEN-NISSAN et al. "Chapter 6: Bioceramics: An Introduction", Engineering Materials for Biomedical Applications Edited by Swee Hin Teoh, Teoh Swee Hin, World Scientific 2004, ISBN:9812560610, pp. 6-17.
TOSHIKI MIYAZAKI et al., Journal of the Ceramic Society of Japan 2001, vol. 109, No. 11, pp. 929-933.
JAPANESE PATENT OFFICE, Office Action in counterpart JP Application Serial No. 2003-184848 issued Nov. 24, 2009, 6 pages.

* cited by examiner

*Primary Examiner*—Carlos A Azpuru
(74) *Attorney, Agent, or Firm*—Wood, Herron & Evans, L.L.P.

(57) ABSTRACT

A coating liquid comprising a polysilazane and a calcium compound is applied to a base material formed from a metal or a ceramic, and the coating liquid is then heated to form a film with apatite forming ability and complete the preparation of a biomaterial. Furthermore, by immersing this biomaterial comprising the film with apatite forming ability in a simulated body fluid, an apatite layer can be formed on top of the film.

6 Claims, 1 Drawing Sheet

BIOMATERIAL HAVING APATITE FORMING ABILITY

BACKGROUND OF THE INVENTION

1. Field of the Invention

The present invention relates to a biomaterial that can be used for artificial bone, artificial teeth roots, and artificial joints and the like, a film with apatite forming ability which covers the surface of this biomaterial, and a coating liquid capable of forming this film.

2. Description of the Related Art

Artificial bone, artificial teeth roots and artificial joints and the like are placed inside living bodies, and must consequently display bioaffinity, in order to prevent being rejected as foreign matter.

The crystalline structure of apatites such as hydroxyapatite $[Ca_{10}(PO_4)_6(OH)_2]$ closely resembles the crystalline structure of biosystems such as bone and teeth, and apatites have been confirmed as displaying good bioaffinity, enabling them to be integrated with biosystems inside living bodies.

Taking advantage of this characteristic, hydroxyapatite is conventionally used to coat the surface of metals such as stainless steel and titanium alloy, or ceramics such as zirconia, which are used as the base materials for biomaterials such as artificial bone, artificial teeth roots, and artificial joints, thereby forming a surface layer that imparts bioaffinity to the biomaterial.

Many methods have been proposed for forming this surface layer of hydroxyapatite on the base material.

A first method is disclosed in Japanese Unexamined Patent Application, First Publication No. Sho 62-34559, and involves coating the hydroxyapatite directly onto the base material using plasma spraying.

A second method is disclosed in Japanese Examined Patent Application, Second Publication No. Hei 2-13580, and comprises a sintering method used in the production of a terminal for use with living organisms.

Furthermore, a third method involves injecting calcium ions into the surface of a titanium base material, and then immersing the base material in a simulated body fluid. In addition, a fourth method involves treating a base material of titanium with a high concentration aqueous alkali solution, conducting subsequent heat treatment at 600° C., and then immersing the base material in a simulated body fluid.

However, in the plasma spraying of the first method described above, the high temperature heat treatment causes the raw material hydroxyapatite to melt, which can result in the formation of a different type of hydroxyapatite, and an undesirable lowering of the bioaffinity. Additional problems also arise in that the formation of a dense layer of hydroxyapatite is difficult, the adhesion between the base material and the hydroxyapatite is poor, leading to very low yields, and the fact that the method requires expensive equipment.

In the second method, namely the sintering method, the high temperature heat treatment causes the raw material hydroxyapatite to melt, which can result in the formation of a different type of hydroxyapatite, and an undesirable lowering of the bioaffinity. Furthermore, in the third method described above, the ion injection of calcium ions requires expensive equipment, and moreover, the surface of the coated base material is prone to distortion and the occurrence of defects. The fourth method requires both treatment with a high concentration aqueous alkali solution, and a high temperature heat treatment, and this takes time and effort, leading to increased costs.

SUMMARY OF THE INVENTION

The present invention aims to resolve the problems associated with the conventional technology described above, with an object of providing a biomaterial that exhibits excellent bioaffinity and for which a film of an apatite such as hydroxyapatite can be readily formed on the surface, a film with apatite forming ability that is used in the formation of the biomaterial, and a coating liquid for producing the film with apatite forming ability, wherein this film with apatite forming ability can be formed through a simple operation, without the use of expensive equipment.

In order to resolve the problems described above, the present invention comprises the following seven aspects, labeled (1) to (7).

(1) A coating liquid capable of forming a film with apatite forming ability, comprising a polysilazane and a calcium compound.

(2) A coating liquid according to aspect (1), wherein the calcium compound is calcium stearoyl lactate.

(3) A coating liquid according to either one of aspect (1) and aspect (2), further comprising fine particles of titanium oxide.

(4) A coating according to any one of aspect (1) through aspect (3), further comprising a medication.

(5) A film with apatite forming ability, which is produced by applying a coating liquid according to any one of aspect (1) through aspect (4).

(6) A biomaterial comprising a base material and a film with apatite forming ability provided on top of the base material, wherein the film is produced by applying a coating liquid according to any one of aspect (1) through aspect (4) to the base material.

(7) A biomaterial comprising a base material, a film with apatite forming ability provided on top of the base material, and an apatite layer formed on top of the film, wherein the film is produced by applying a coating liquid according to any one of aspect (1) through aspect (4) to the base material, and the apatite layer is formed by contacting the film with a simulated body fluid.

According to the present invention, a biomaterial that exhibits excellent bioaffinity and for which a film of an apatite can be readily formed on the surface, a film with apatite forming function that is used in the formation of the biomaterial, and a coating liquid that is used for producing the film with apatite forming ability can be obtained. Furthermore, the film with apatite forming ability can be formed through a simple operation, without the use of expensive equipment.

DETAILED DESCRIPTION OF THE INVENTION

Figure 1:
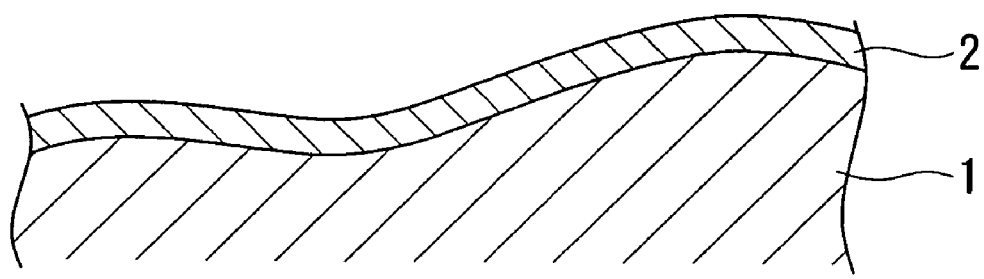
FIG. 1 is a schematic cross-sectional view showing a first example of a biomaterial of the present invention.

As follows is a more detailed description of the present invention.

First is a description of a coating liquid of the present invention.

A coating liquid of the present invention is a coating liquid that when applied, produces a film with apatite forming ability, and is a solution or a dispersion comprising a polysilazane and a calcium compound as essential components.

The polysilazane can be a straight chain polysilazane or a cyclic polysilazane. Examples of suitable straight chain polysilazanes include perhydropolysilazane, polymethylhydrosilazane, poly(N-methylsilazane), poly(N-(triethylsilyl)allylsilazane), poly(N-(dimethylamino)cyclohexylsilazane), and phenylpolysilazane. Any of these polysilazanes can be used, and the above list is no way restrictive. Furthermore, the polysilazane used may be either a single polysilazane, or a mixture of two or more different polysilazanes. A specific example of a commercial polysilazane that can be used is "TONEN POLYSILAZANE", manufactured by Tonen-General Sekiyu K. K.

This polysilazane is used in solution, and suitable solvents include aromatic hydrocarbons, aliphatic hydrocarbons, alicyclic hydrocarbons, halogenated hydrocarbons and ethers. Examples of suitable aromatic hydrocarbons include benzene, toluene, xylene and ethylbenzene. Examples of suitable aliphatic hydrocarbons include pentane, hexane, isohexane, methylpentane, heptane, isoheptane, octane and isooctane. Examples of suitable alicyclic hydrocarbons include cyclopentane, methylcyclopentane, cyclohexane and methylcyclohexane.

Examples of suitable halogenated hydrocarbons included halogenated methanes, halogenated ethanes and halogenated benzenes. Specific examples include methylene chloride, chloroform, carbon tetrachloride, bromoform, ethylene chloride, ethylidene chloride and trichloroethane. Examples of suitable ethers include halogenated ethers, aliphatic ethers and alicyclic ethers. Specific examples include ethyl ether, isopropyl ether, ethyl butyl ether, butyl ether, 1,2-dioxyethane, dioxane, dimethyldioxane, tetrahydrofuran and tetrahydropyran. The above list of solvents is in no way restrictive. These solvents can be used singularly, or in combinations of two or more solvents.

The concentration of the polysilazane within the solution is typically within a range from 0.05 to 50% by weight, and preferably from 1 to 20% by weight.

Examples of the other essential component of the coating liquid, namely the calcium compound, include both organic and inorganic calcium compounds. Specific examples of suitable organic calcium compounds include calcium fatty acid esters such as calcium stearoyl lactate and calcium stearate, as well as diethyl calcium, calcium oxalate, calcium lactate, calcium gluconate and calcium acetate. Specific examples of inorganic calcium compounds include tricalcium phosphate, apatite and calcium carbonate. Preferred materials include calcium stearoyl lactate, tricalcium phosphate and apatite. Of these, calcium stearoyl lactate, which is soluble in the polysilazane solvent and is a certified food additive, is particularly preferred.

The calcium compound is either dissolved in a solvent to form a solution, or used as a suspended dispersion. Calcium compounds that are not dissolved in a solvent are preferably in the form of fine particles, with a particle size of no more than 1 µm, and preferably no more than 0.1 µm, in order to improve the stability of the suspension.

There are no particular restrictions on the quantity of the calcium compound, although the quantity is preferably within a range from 0.1 to 90 parts by weight, and even more preferably from 1 to 50 parts by weight, per 100 parts by weight of the polysilazane.

In addition to the polysilazane and the calcium compound, other additives may also be added to the coating liquid.

Examples of possible additives include any of the variety of available fillers. Such fillers include alumina, silica, titanium and alloys thereof, titanium compounds such as titanium oxide, zinc oxide, zirconium oxide, cerium oxide, magnesium carbonate, magnesium hydrogencarbonate, glass or ceramics, talc, mica, kaolin, nylon powder, polyethylene powder, fluororesin powder, polymethyl methacrylate powder, polyurethane powder, polystyrene powder, polyester powder, silicon resin powder, boron nitride and bismuth oxychloride. Of these fillers, fine particles of titanium oxide with a particle size of 5 to 500 nm are preferred, and by using such fine titanium oxide particles, the apatite forming ability can be improved.

Other possible additives include bone-inducing agents such as bone-forming proteins, anticancer agents such as Melphalan, as well as other medications such as Cytokine. Addition of these types of materials enables the formation of biomaterials with enhanced physiological activities such as increased bone forming function or anticancer properties.

A coating liquid of the present invention may be a solution produced by adding and dissolving the calcium compound in the organic solvent solution of the polysilazane, a dispersion produced by adding and dispersing the calcium compound in the organic solvent solution of the polysilazane, or a liquid produced by mixing the polysilazane solution with a solution or a dispersion of the calcium compound produced by dissolving or dispersing the calcium compound in a solvent. The additives such as the fillers described above can either be added to the polysilazane solution, added to the solution or dispersion of the calcium compound, or added to a mixed liquid of the polysilazane solution and the solution or dispersion of the calcium compound.

Next is a description of a film with apatite forming ability according to the present invention.

This film is produced by applying a coating liquid described above, and then solidifying the liquid by drying, calcination, or irradiation with ultraviolet radiation. Examples of suitable coating materials to which the coating liquid can be applied, in addition to the biomaterial base materials described below, include glass plates, metal plates, plastic sheets, and ceramic plates. If the coating liquid is applied to one of these coating materials other than a biomaterial base material, then the generated film is removed from the coating material, and either used, as is, as a film with a variety of functions, or bonded to a biomaterial base material or some other material.

Examples of suitable methods of applying the coating liquid include spin coating methods, flow coating methods, spraying methods, dipping methods, brush coating methods, or immersion methods. The temperature used to dry the coating liquid following application may be any temperature sufficient to cause evaporation of the solvent, and can be selected in accordance with the type of solvent used, the material being coated, and the purpose of the application. The coating liquid may be simply dried after application, but may also be heated, either without drying or following the drying process, or irradiated with ultraviolet radiation.

The heating conditions can be adjusted as desired to conform with the type of solvent used, the type of base material, and the purpose of the application, although heating at a temperature within a range from room temperature to 900° C. for a period of 0.1 to 6 hours is preferred, and heating at a temperature from 90 to 600° C. for a period of 0.5 to 4 hours is even more desirable.

The thickness of a film produced in this manner is typically within a range from 0.01 to 20 µm, and preferably from 0.1 to 5 µm, although this range is in no way restrictive.

During the drying or heating process following the application of the coating liquid, the polysilazane within the film reacts with the moisture and the oxygen in the atmosphere and is converted to a silica that contains ≡SiOH groups and —SiO— groups, and calcium ions are incorporated within these silica molecules. The ≡SiOH groups and calcium ions within the silica function as growth starting points (growth nuclei) for apatites such as hydroxyapatite, ensuring a film with good apatite forming ability. Furthermore, if fine particles of a filler such as titanium oxide are dispersed finely within the film, then these fine particles also function as growth starting points for apatites.

Next is a description of a biomaterial of the present invention.

As shown in FIG. 1, a first example of a biomaterial of the present invention comprises a base material 1, and a film 2 with apatite forming ability formed thereon.

Examples of suitable materials for the base material 1 include metals and alloys such as stainless steel, titanium alloy and cobalt-chromium-molybdenum alloy, ceramics such as zirconia and alumina, and plastics such as ultra high molecular weight polyethylene. There are no particular restrictions on the base material, and ideal materials include those materials used in fields requiring good bioaffinity. The types of metals, alloys, ceramics and plastics used for artificial bone, artificial teeth roots, fillers for bone loss, artificial joints, blood filters and catheters are particularly suitable.

The shape of the base material 1 is arbitrary, and may be plate shaped, spherical, cylindrical, hollow cylinder shaped, fiber-like, or in the form of a porous structure. The shape will vary depending on the intended use, with fiber-like forms or porous structures being ideal for blood filters, and hollow cylindrical shapes being ideal for catheters. Similarly, appropriate shapes can be selected for other applications such as artificial bone, artificial teeth roots, bone loss, or artificial joints. Needless to say, the shape of a base material with a film with apatite forming ability formed thereon can be adapted to suit the intended use or purpose of the biomaterial.

The film 2 on top of this base material 1 is a film with apatite forming ability produced by applying a coating liquid described above to the surface of the base material 1. The method of applying and subsequently solidifying the coating liquid, and the thickness of the film 2 can be the same as described above for the films with apatite forming ability.

In a modification of this first example, an intermediate layer can be provided between the base material 1 and the film 2 with apatite forming ability, to improve the bonding between the two layers. Suitable examples of this intermediate layer include films with a thickness of 0.01 to 2 μm produced by applying a solution of a polysilazane that is either the same as, or different from, the polysilazane of the coating liquid described above, and then conducting heating. The intermediate layer may be either a single layer or a plurality of layers, depending on the intended use of the biomaterial.

In a biomaterial of this first example, a film 2 with good apatite forming ability is provided on the surface, and consequently when the biomaterial is implanted inside a living body as an artificial bone, an artificial tooth root or an artificial joint, the film 2 contacts the bodily fluids inside the body, apatite such as hydroxyapatite begins to form at the apatite growth starting points on the film 2, and this apatite grows to rapidly form an apatite layer on the surface of the film 2, thereby ensuring good bioaffinity.

Figure 2:
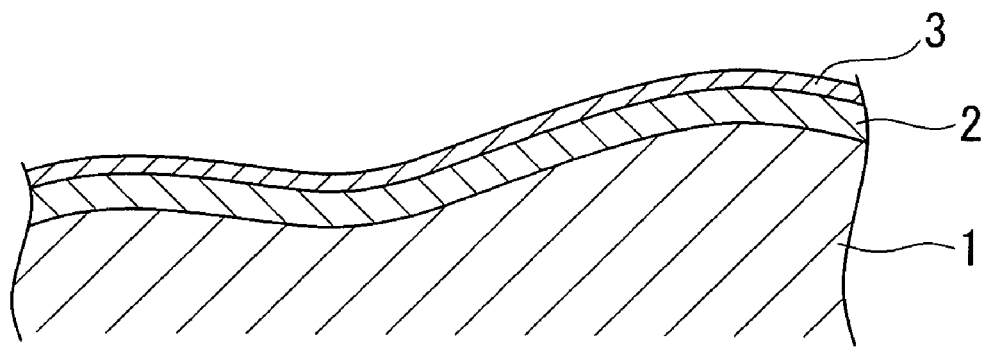
FIG. 2 is a schematic cross-sectional view showing a second example of a biomaterial of the present invention.

As shown in FIG. 2, a second example of a biomaterial of the present invention comprises a film 2 with apatite forming ability provided on top of a base material 1, with an additional layer 3 formed from apatite provided on top of the film 2. Furthermore, as in the previous example, an intermediate may also be provided between the base material 1 and the film 2, if required.

The base material 1 and the film 2 with apatite forming ability are the same as those described above for the first example, and so further description is omitted here.

The formation of the layer 3 of apatite on top of the film 2 with apatite forming ability is achieved by firstly preparing a biomaterial of the configuration of the first example, and then bringing this biomaterial into contact with a simulated body fluid, by immersion in the body fluid, for example. The simulated body fluid comprises the same inorganic ions as human body fluids, and the concentration of those inorganic ions are also substantially equal with those of human body fluids. Specific examples of suitable simulated body fluids include the inorganic ion compositions used in the examples described below.

The conditions under which the biomaterial contacts the simulated body fluid include a temperature of 35 to 38° C., and a contact period of 1 hour to 30 days, and contact with the simulated body fluid is preferably continued until essentially the entire surface of the film 2 is completely covered with apatite. Formation of the layer 3 of apatite on the surface of the film 2 can be continued until the presence of the layer can be confirmed visually.

In a biomaterial of this second example, a layer 3 formed from apatite is preformed on the surface of the biomaterial, and consequently when the biomaterial is implanted inside a living body, it exhibits a good level of bioaffinity immediately, and is rapidly integrated into the biosystem.

EXAMPLES

As follows is a more specific description of the present invention based on a series of examples, although the present invention is in no way restricted to the examples presented here.

Example 1

A 5 wt % solution of perhydropolysilazane was applied to a base material comprising a stainless steel plate (SUS304, 20×20×0.1 mm) using a flow coating method, and the coating was then dried for 30 minutes and then heated at 300° C. for 1 hour to form an intermediate layer.

Meanwhile, a coating liquid was prepared by mixing 3 cm$^3$ of a xylene solution containing 0.03 g of dissolved calcium stearoyl lactate with 2 cm$^3$ of a 5 wt % solution of perhydropolysilazane.

Using a flow coating method, the coating liquid was applied to the base material on which the intermediate layer had been formed, as a second layer. The coating was then dried at 30° C. (room temperature) for 30 minutes, heated at 300° C. for 1 hour, and then allowed to cool naturally to room temperature, thereby forming a film with apatite forming ability and completing the preparation of a biomaterial test specimen.

This test specimen was immersed in 50 ml of a simulated body fluid of the composition shown below, and allowed to stand for 10 days in a constant temperature bath maintained at 36.5° C. to test for the formation of an apatite layer on the surface film of the test specimen.

Following completion of the immersion process, the test specimen was removed from the simulated body fluid, washed with distilled water, and dried at room temperature. The flow coating method described above is a method in which rather than applying the entire solution to the base material, only an appropriate quantity is applied to the surface of the base material.

Example 2

With the exception of mixing and dispersing tricalcium phosphate in xylene instead of dissolving calcium stearoyl lactate as in the example 1, preparations were performed in the same manner as the example 1.

Example 3

With the exception of mixing and dispersing hydroxyapatite powder in xylene instead of dissolving calcium stearoyl lactate as in the example 1, preparations were conducted in the same manner as the example 1.

Comparative Examples 1 to 3

With the exception of not adding the calcium compound in each of the examples 1 to 3, preparations were conducted in the same manner as the examples 1 to 3 respectively.

<Preparation of the Simulated Body Fluid>

A simulated body fluid with inorganic ion concentrations substantially equal to those of human body fluids ($Na^+$: 142.0 mM, $K^+$: 5.0 mM, $Mg^{2+}$: 1.5 mM, $Ca^{2+}$: 2.5 mM, $Cl^-$: 147.8 mM, $HCO_3^-$: 4.2 mM, $HPO_4^{2-}$: 1.0 mM, $SO_4^{2-}$: 0.5 mM) was prepared in the following manner.

Suitable quantities of NaCl, $NaHCO_3$, KCl, $K_2HPO_4.3H_2O$, $MgCl_2.6H_2O$, $CaCl_2$ and $Na_2SO_4$ were dissolved, in a predetermined sequence, in ultra pure water maintained at 36.5° C. to achieve the predetermined concentrations of each ion. Finally, trishydroxymethylaminomethane (($CH_2OH)_3CNH_2$) and 1 M HCl were used to adjust the pH to 7.40 as measured by a pH meter.

<Visual Evaluation of the Test Specimen Surface>

The level of apatite deposition on the surface of the test specimens following immersion in the simulated body fluid was evaluated by visual inspection, and recorded using the following scale.

O: Deposition across the entire surface

Δ: Partial deposition x: No deposition

The result for each example is shown below in Table 1.

From the results in Table 1 it is evident that the test specimens provided with a film produced by applying a coating liquid comprising a polysilazane and a calcium compound displayed good deposition of apatite on the surface of the film, confirming that these films have a good apatite forming ability.

Films with apatite forming ability according to the present invention can be used in materials in a variety of fields including medical treatment materials, dental materials, cosmetic materials, food additive materials, materials for fixing enzyme, protein or DNA, gas adsorption materials, and bioreactor materials, as well as in electrolytic films for fuel cells, diaphragms, stainproofing agents, surface coatings for contact lenses, and on the surfaces of ornaments and jewelry that contact the skin such as pierced jewelry and ear rings. Furthermore, materials comprising this type of film with apatite forming ability provided on the surface can be used as medical treatment materials, dental materials, cosmetic materials, food additive materials, materials for fixing enzyme, protein, DNA or biochips, gas adsorption materials and bioreactor materials.

What is claimed is:

1. A biomaterial having an apatite forming ability, comprising:
    a base material and
    a film provided on top of said base material,
    wherein said film is produced by a process which comprises steps of
        applying a coating liquid to said base material, and
        solidifying said coating liquid by drying, calcinations, or irradiation with ultraviolet radiation,
    wherein said coating liquid comprises
        a solvent,
        a polysilazane, which is dissolved in said solvent, and
        a calcium compound, which is dissolved in said solvent or disperses in the form of fine particles with a particle size of no more than 1 μm in said solvent, within a range from 0.1 to 90 parts by weight per 100 parts by weight of said polysilazane.

2. The biomaterial according to claim 1, wherein said calcium compound is calcium stearoyl lactate.

3. The biomaterial according to claim 1, wherein said coating liquid further comprises fine particles of titanium oxide.

TABLE 1

| | First layer | Polysilazane 5% PHPS solution | Second layer | | | Result |
|---|---|---|---|---|---|---|
| | | | Calcium compound | | | |
| | | | Calcium stearoyl lactate/ xylene | Tricalcium phosphate/ xylene | HAP/xylene | |
| Example 1 | $SiO_2$ | 2 cm³ | 0.03 g/3 cm³ | — | — | o |
| Example 2 | $SiO_2$ | 2 cm³ | — | 0.03 g/3 cm³ | — | o |
| Example 3 | $SiO_2$ | 2 cm³ | — | — | 0.03 g/3 cm³ | o |
| Comparative example 1 | $SiO_2$ | 2 cm³ | — | — | — | x |
| Comparative example 2 | $SiO_2$ | 2 cm³ | — | — | — | x |
| Comparative example 3 | $SiO_2$ | 2 cm³ | — | — | — | x |

PHPS: perhydropolysilazane
HAP: fine particles of hydroxyapatite

4. The biomaterial according to claim 1, wherein said coating liquid further comprises a medication.

5. The biomaterial according to claim 1, wherein apatite is formed on a portion of a surface of the film of the biomaterial when the biomaterial is immersed in a simulated body fluid.

6. The biomaterial according to claim 5, wherein apatite is formed across the entire surface of the film of the biomaterial when the biomaterial is immersed in the simulated body fluid.

* * * * *